United States Patent
Jin et al.

(10) Patent No.: US 9,796,895 B2
(45) Date of Patent: Oct. 24, 2017

(54) METHOD OF USING A CARBON-MICHAEL COMPOUND

(71) Applicant: Dow Global Technologies LLC, Midland, MI (US)

(72) Inventors: Xin Jin, Lake Jackson, TX (US); Dwight Latham, Clute, TX (US); Steven Crain, Midland, MI (US); Mark Sonnenschein, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 155 days.

(21) Appl. No.: 14/426,805

(22) PCT Filed: Sep. 26, 2013

(86) PCT No.: PCT/US2013/062000
§ 371 (c)(1),
(2) Date: Mar. 9, 2015

(87) PCT Pub. No.: WO2014/052644
PCT Pub. Date: Apr. 3, 2014

(65) Prior Publication Data
US 2015/0218431 A1    Aug. 6, 2015

Related U.S. Application Data

(60) Provisional application No. 61/706,360, filed on Sep. 27, 2012.

(51) Int. Cl.
| | |
|---|---|
| *C08G 61/12* | (2006.01) |
| *C09K 5/08* | (2006.01) |
| *C08J 9/14* | (2006.01) |
| *C07C 69/73* | (2006.01) |
| *C08G 18/32* | (2006.01) |
| *C08G 18/34* | (2006.01) |

(52) U.S. Cl.
CPC ............ *C09K 5/08* (2013.01); *C07C 69/73* (2013.01); *C08G 18/3206* (2013.01); *C08G 18/348* (2013.01); *C08G 61/128* (2013.01); *C08J 9/14* (2013.01); *C08J 9/146* (2013.01); *C08J 2203/14* (2013.01); *C08J 2203/142* (2013.01); *C08J 2203/144* (2013.01); *C08J 2203/162* (2013.01); *C08J 2205/06* (2013.01); *C08J 2333/06* (2013.01)

(58) Field of Classification Search
CPC ............ C08G 61/128; C08G 2261/30; C08G 2261/31; C08G 2261/312; C08G 2261/33–2261/3342; B32B 25/045; B32B 27/065; B32B 27/28; B32B 2266/0207–2266/0214; B32B 2307/102; B32B 2307/304–2307/308
See application file for complete search history.

(56) References Cited

U.S. PATENT DOCUMENTS

| | | |
|---|---|---|
| 2005/0081994 A1 | 4/2005 | Beckley et al. |
| 2005/0245721 A1* | 11/2005 | Beckley ............... C08G 61/12 528/271 |
| 2006/0047010 A1 | 3/2006 | O'Leary |
| 2006/0247374 A1 | 11/2006 | Beckley et al. |
| 2007/0173602 A1 | 7/2007 | Brinkman et al. |
| 2008/0281006 A1 | 11/2008 | O'Leary et al. |

FOREIGN PATENT DOCUMENTS

| | | |
|---|---|---|
| EP | 1435383 | 7/2004 |
| EP | 1462501 | 9/2004 |

OTHER PUBLICATIONS

Stanley, F. E.; Warner, A. M.; Schneiderman, E.; Salcup, A. M. Rapid determination of surfactant critical micelle concentrations using pressure-driven flow with capillary electrophoresis instrumentation. J. Chromatogr. A. 2009, vol. 1216, 47, pp. 8431-8434.*
D.K. Chattopadhyay, et al., Progess in Polymer Science (2009), 34 (10), pp. 1068-1133.

* cited by examiner

*Primary Examiner* — Robert C Boyle
*Assistant Examiner* — Stephen Rieth
(74) *Attorney, Agent, or Firm* — Brooks, Cameron & Huebsch, PLLC

(57) ABSTRACT

Embodiments of the present disclosure are directed towards using a carbon-Michael compound. As an example, a method of using a carbon-Michael compound to reduce heat transfer can include locating the carbon-Michael compound between a heat provider and a heat receptor, where the carbon-Michael compound is a reaction product of a multifunctional acrylate compound with a multifunctional Michael donor, and the heat provider has a temperature from 100 C to 290 C.

8 Claims, No Drawings

METHOD OF USING A CARBON-MICHAEL COMPOUND

This application is a National Stage Application under 35 U.S.C. §371 of International Application Number PCT/US2013/062000, filed Sep. 26, 2013 and published as WO 2014/052644 on Apr. 3, 2014, which claims the benefit to U.S. Provisional Application 61/706,360, filed Sep. 27, 2012, the entire contents of which are incorporated herein by reference in its entirety.

FIELD OF DISCLOSURE

Embodiments of the present disclosure are using a carbon-Michael compound, more specifically, embodiments are directed towards using a carbon-Michael compound to reduce heat transfer.

BACKGROUND

Michael reactions, which may also be referred to as conjugate additions, are utilized for polymer synthesis. For example, Michael reactions can provide for step growth and/or chain growth polymerization and have been utilized in the synthesis of linear, graft, hyper-branched, dendritic and network polymers.

A Michael reaction involves the addition of a nucleophile, which may be referred to as a Michael donor, to an electrophile, which may be referred to as a Michael acceptor. Some Michael reactions, e.g., a carbon-Michael reaction, can provide a carbon-carbon bond.

Some polymers formed from a Michael reaction have been employed in applications where it is desirable to have little or no isocyanate-containing compounds. For example, polymeric foams formed from a Michael reaction have been utilized to replace some polyurethane foams that are formed from an isocyanate-terminated compound and an isocyanate-reactive material.

SUMMARY

The present disclosure provides methods of using a carbon-Michael compound to reduce heat transfer. Methods of using the carbon-Michael compound to reduce heat transfer can include locating the carbon-Michael compound between a heat provider and a heat receptor, where the carbon-Michael compound is a reaction product of a multifunctional acrylate compound with a multifunctional Michael donor, and the heat provider has a temperature from 100° C. to 290° C.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Methods of using a carbon-Michael compound are described herein. Surprisingly, it has been found that the carbon-Michael compounds discussed herein can be utilized in high temperature applications. Advantageously it has been found that the carbon-Michael compounds discussed herein have thermal degradation temperatures that help provide that they are suitable for high temperature applications. Additionally, it has been found that the carbon-Michael compounds discussed herein have storage modulus from 30 megapascal (MPa) to 1000 MPa at a high temperature (e.g., at 200° C.), which are desirable for certain applications discussed herein.

As disclosed herein, the carbon-Michael compounds discussed herein can be used to reduce heat transfer. The method of using the carbon-Michael compound to reduce heat transfer can include locating the carbon-Michael compound between a heat provider and a heat receptor, where the heat provider has a temperature from 100 degrees Celsius (° C.) to 290° C.

The methods disclosed herein include a carbon-Michael compound. The carbon-Michael compound can be formed from a Michael reaction. As mentioned, some Michael reactions, e.g., a carbon-Michael reaction, can provide a carbon-carbon bond. The Michael reaction involves the addition of a nucleophile, which may be referred to as a Michael donor, to an electrophile, which may be referred to as a Michael acceptor. The Michael donor can be a multifunctional Michael donor. As used herein, a "multifunctional carbon-Michael donor" is a material that contains one or more carbon-Michael donor functionalities and can react with two or more carbon-Michael acceptor functionalities to form a carbon-carbon bond to each of the carbon-Michael acceptor functionalities. As used herein, Michael donor functionalities are groups that in the presence of a carbon-Michael reaction catalyst form a carbanion that reacts with the carbon-carbon double or triple bond of a Michael acceptor group to form a carbon-carbon bond to the Michael acceptor group.

The Michael donor can be an acetoacetate compound, e.g., a multifunctional acetoacetate compound. The Michael acceptor can be an acrylate compound, e.g., a multifunctional acrylate compound. The carbon-Michael compound can be a reaction product of a multifunctional acrylate compound with a multifunctional Michael donor.

As mentioned, the multifunctional Michael acceptor can be an acrylate compound. As used herein "acrylate" includes acrylates and (meth)acrylates. While not being bound to theory, Michael acceptor functionalities, for purposes of this disclosure, refer to an activated alkene having an aliphatic carbon-carbon double or triple bond alpha to a carbonyl (an "enone" group) or, a nitro group. The multifunctional acrylate compound can have two (2) Michael acceptor functionalities to ten (10) Michael acceptor functionalities. For example, the multifunctional acrylate compound can have 2, 3, 4, 5, 6, 7, 8, 9, or 10 Michael acceptor functionalities.

Examples of the multifunctional acrylate compound include, but are not limited to, bisphenol A epoxy diacrylate, bisphenol A glycerolate (1 glycerol/phenol) diacrylate, 1,4-butanediol diacrylate, 1,6-hexanediol diacrylate, neopentyl glycol diacrylate, diethylene glycol diacrylate, triethylene glycol diacrylate, tetraethylene glycol diacrylate, polyethylene glycol diacrylate, dipropylene glycol diacrylate, tripropylene glycol diacrylate, cyclohexane dimethanol diacrylate, alkoxylated hexanediol diacrylate, alkoxylated cyclohexane dimethanol diacrylate, propoxylated neopentyl glycol diacrylate, trimethylolpropane triacrylate, ethoxylated trimethylolpropane triacrylate, propoxylated trimethylolpropanetriacrylate, acrylated polyester oligomer, bisphenol A diacrylate, acrylated bisphenol A diglycidylether, ethoxylated bisphenol A diacrylate, tris(2-hydroxyethyl)isocyanurate triacrylate, acrylated aliphatic urethane oligomer, acrylated aromatic urethane oligomer, acrylated polyester oligomer, or a combination thereof, among others. One or more embodiments of the present disclosure provide the multifunctional acrylate compound is selected from the group of trimethylolpropanetriacrylate, pentaerythritoltetraacrylate, di-trimethylolpropanetertraacrylate, di-pentaerythritolhexaacrylate, di-pentaerthritolpentaacrylate, diacrylate of diglycidyl ether bisphenol-A, ethoxylated trimethylolpropane triacrylate, tricyclodecanedimethanol diacrylate, and cyclohexanedimethanol diacrylate, or a combination thereof.

As mentioned, the carbon-Michael compound can be a reaction product of the multifunctional acrylate compound with a multifunctional Michael donor. While not being bound to theory, a functionality for a multifunctional Michael donor, for purposes of this disclosure, are groups that in the presence of a carbon-Michael reaction catalyst to form a carbanion that reacts with the carbon-carbon double or triple bond of a Michael acceptor group to form a carbon-carbon bond to the Michael acceptor group.

The multifunctional Michael donor can be an ester of an alcohol, such as methanol, ethanol, teriary butanol, and 2-hydroxyethyl (meth)acrylate, among others. The ester can be an acetoacetate ester, a cyanoacetate ester, a malonic acid ester, or a combination thereof, among other esters. Examples of the ester include, but are not limited to, tert-butyl 3-oxobutyrate, esters of polyhydric alcohols such as ethylene glycol, 1,2- or 1,3-propane diol, 1,4-butane diol, 1,2-butanediol, 1,6-hexanediol, neopentyl glycol, 2-methyl-1,3-propane diol, diethylene glycol, triethylene glycol, dipropylene glycol, tripropylene glycol, poly(propylene glycol), poly(ethylene glycol), cyclohexanedimethanol, trimethylol propane, triethylol propane, pentaerythritol, glycerin, glycerol, dipentaerythritol, di-trimethylolpropane, glucose, isosorbide, butyl ethyl propanediol, esters derived from polyester polyols, polyether polyols, or polyesteramide polyols, or a combination thereof, among others. The multifunctional Michael donor can be a multifunctional acetoacetate compound. The multifunctional acetoacetate compound is selected from the group of acetoacetates derived from glycerol, trimethylolpropane, ethanol isosorbide, neopentylglycol, pentaerythritol, di-methylolpropane, pentaerythritol, di-pentaerythritol, propoxylated monosaccharides, trimethylol ethane, or a combination thereof.

The multifunctional acrylate compound and the multifunctional Michael donor can be reacted in a molar ratio of 0.5:3.0 to 3.0:0.5 (moles of multifunctional acrylate compound functionalities to moles of the Michael donor functionalities). All individual values and subranges from and including 0.5:3.0 to 3.0:0.5 moles of multifunctional acrylate compound functionalities to moles of the Michael donor functionalities are included herein and disclosed herein; for example, the multifunctional acrylate compound and the multifunctional Michael donor can be reacted in a molar ratio with a upper limit of 3.0:0.5, 2.8:0.5, or 2.6:0.5 to a lower limit of 0.5:3.0, 0.7:3.0, or 1.0:3.0 moles of multifunctional acrylate compound functionalities to moles of the Michael donor functionalities.

The multifunctional acrylate compound and the multifunctional Michael donor can be reacted in the presence of a carbon-Michael catalyst, e.g., when forming the carbon-Michael compound. As an example, the catalyst can include tertiary amine compounds, amidine compounds, quaternary ammonium hydroxides, alkali metal hydroxides, alkali metal alkoxides, alkali metal acetylacetonates, quaternary ammonium acetylacetonates, among others. Examples of the catalyst include, but are not limited to, tetramethyl ammonium hydroxide, tetraethyl ammonium hydroxide, tetrabutyl ammonium hydroxide, tetraoctyl ammonium hydroxide, trimethylamine, triethylamine, N-methylmorpholine, N-ethylmorpholine, N,N-dimethylbenzylamine, N,N-dimethylethanolamine, N,N,N',N'-tetramethyl-1,4-butanediamine, N,N-dimethylpiperazine, 1,4-diazobicyclo-2,2,2-octane, bis(dimethylaminoethyl)ether, bis(2-dimethylaminoethyl) ether, morpholine, 4,4'-(oxydi-2,1-ethanediyl)bis, triethylenediamine, pentamethyl diethylene triamine, dimethyl cyclohexyl amine, N-cetyl N,N-dimethyl amine, N-cocomorpholine, N,N-dimethyl aminomethyl N-methyl ethanol amine, N,N,N'-trimethyl-N'-hydroxyethyl bis(aminoethyl) ether, N,N-bis(3-dimethylaminopropyl)N-isopropanolamine, (N,N-dimethyl)amino-ethoxy ethanol, N,N,N',N'-tetramethyl hexane diamine, N,N-dimorpholinodiethyl ether, N-methyl imidazole, dimethyl aminopropyl dipropanolamine, bis(dimethylaminopropyl)amino-2-propanol, tetramethylamino bis(propylamine), (dimethyl(aminoethoxyethyl))((dimethyl amine)ethyl)ether, tris(dimethylamino propyl)amine, dicyclolicxyl methyl amine, bis(N,N-dimethyl-3-aminopropyl)amine, 1,2-ethylene piperidine, methyl-hydroxyethyl piperazine, or a combination thereof, among others. One or more embodiments of the present disclosure provide the catalyst is selected from the group of 1,1,3,3-tetramethylguanidine, 1,8-diazabicyclo[5.4.0]undec-7-ene, 1,5-diazabicyclo[4.3.0]non-5-ene, tetramethylammonium hydroxide, (2 hydroxyethyl)trimethylammonium hydroxide, potassium carbonate, potassium phosphate, potassium phenoxide, sodium phenoxide, tetraethylammonium hydroxide, or a combination thereof.

The catalyst can have a concentration of 0.001 moles of catalyst per equivalent of multifunctional Michael donor to 1 mole of catalyst per equivalent of multifunctional Michael donor. All individual values and subranges from and including 0.001 moles of catalyst per equivalent of multifunctional Michael donor to 1 mole of catalyst per equivalent of multifunctional Michael donor are included herein and disclosed herein; for example the catalyst can have a concentration with a lower limit of 0.001 moles, 0.002 moles, or 0.003 moles of catalyst per equivalent of multifunctional Michael donor to an upper limit of 1 mole, 0.98 moles, or 0.95 moles of catalyst per equivalent of multifunctional Michael donor.

The multifunctional acrylate compound and the multifunctional Michael donor can be reacted in the presence of a blowing agent, e.g., when forming the carbon-Michael compound. The blowing agent can include pentanes, fluorinated hydrocarbons, chlorofluorinated hydrocarbons, formate esters, carbon dioxide, hydrofluoroolefins, hydrochlorofluoroolefins, or a combination thereof, among others. One or more embodiments of the present disclosure provide the blowing agent is selected from the group of cyclopentane, n-pentane, formaldehyde dimethylacetal, methylformate, methyl butane, 1,1,2,2,3-pentafluoropropane, 1,1,1,3,3-pentafluoropropane, 1,1,1,3,3-pentafluorobutane, 1,1,1,2,3,4,4, 5,5,5-decafluoropentane, cis-1,1,1,4,4,4-hexafluorobut-2-ene, trans-1-chloro-3,3,3-trifluoropropene, or a combination thereof.

The blowing agent can have a concentration of 0.5 weight percent to 50 weight percent catalyst based upon a total weight of the multifunctional Michael donor and the multifunctional acrylate compound. All individual values and subranges from and including of 0.5 weight percent to 50 weight percent catalyst based upon a total weight of the multifunctional Michael donor and the multifunctional acrylate compound are included herein and disclosed herein; for example the blowing agent can have a concentration with a lower limit of 0.5 weight percent, 1.0 weight percent, or 1.5 weight percent to an upper limit of 50 weight percent, 48 weight percent, or 45 weight percent blowing agent based upon a total weight of the multifunctional Michael donor and the multifunctional acrylate compound.

The multifunctional acrylate compound and the multifunctional Michael donor can be reacted in the presence of a surfactant, e.g., when forming the carbon-Michael compound. Examples of the surfactant include, but are not limited to, polyalkylene oxides and silicone based interfacial agents, such as organosilicone surfactants. Polyalkylene oxides, for example, can include random and/or block copolymers of ethylene and propylene oxides or ethylene and butylenes oxides, among others. An example of a polyalkylene oxide surfactant is a polyethylene oxide-co-butylene oxide triblock organic surfactant, which is sold under the trade name VORASURF™ 504 (available from The Dow Chemical Company). Examples of organosilicone surfactants include, but are not limited to, polysiloxane/polyether copolymers such as Tegostab™ (available from Evonik Industries), B-8462 and B8469, DABCO™ DC-198 surfactant (available from Air Products and Chemicals), and Niax™ L-5614 surfactant (available from Momentive Performance Products).

The surfactant can have a concentration of 0.1 weight percent to 5.0 weight percent based upon a total weight of the multifunctional Michael donor and the multifunctional acrylate compound. All individual values and subranges from and including of 0.1 weight percent to 5.0 weight percent based upon a total weight of the multifunctional Michael donor and the multifunctional acrylate compound are included herein and disclosed herein; for example the surfactant can have a concentration with a lower limit of 0.1 weight percent, 0.2 weight percent, or 0.3 weight percent to an upper limit of 5.0 weight percent, 4.8 weight percent, or 4.5 weight percent based upon a total weight of the multifunctional Michael donor and the multifunctional acrylate compound.

The carbon-Michael compound can also include one or more additives. Examples of the one or more additives include, but are not limited to, plasticizers, fillers, colorants, preservatives, odor masks, flame retardants, biocides, antioxidants, UV stabilizers, antistatic agents, foam cell nucleators, among others. Concentrations of the one or more additives in the carbon-Michael compound may have differing values for various applications.

The carbon-Michael compound can be in the form of a foam. For example, the carbon-Michael compound can be in the form of a solid foam, e.g., a closed-cell foam. Foams are dispersions in which a gas is dispersed in a liquid material, a solid material, or a gel material. Solid foams include closed-cell foams and open-cell foams.

In closed-cell foam, the gas forms discrete pockets, where the discrete pockets are completely surrounded by the solid material. The closed cells may be referred to as non-intercommunicating. Additionally, the closed cells help to prevent passage of gases or liquids through the closed-cell foam. In contrast to closed-cell foam, in an open-cell foam the gas pockets connect with each other. The open cells may be referred to as intercommunicating.

Generally, the foams can be produced by mixing liquids or low-melting precursor materials, which simultaneously react and expand to form a polymeric foam. The carbon-Michael foam precursor materials include multifunctional Michael donors, Michael acceptors, carbon-Michael catalysts, blowing agents, surfactants and other foam additives.

Embodiments of the present disclosure include locating the carbon-Michael compound between a heat provider and a heat receptor. According to a number of embodiments the carbon-Michael compound can be located, e.g., placed, on the heat provider and/or on the heat receptor. The carbon-Michael compound can be located between the heat provider and the heat receptor such that the carbon-Michael compound contacts a portion of the heat provider and/or contacts a portion of the heat receptor. For example, the carbon-Michael compound can be located to coat, e.g., line, a portion of the heat provider and/or a portion of the heat receptor.

The carbon-Michael compound can be located between the heat provider and the heat receptor such that the carbon-Michael compound does not contact the heat provider and does not contact the heat receptor. The carbon-Michael compound, which is located between the between the heat provider and the heat receptor can be attached to one or more substrates. For example, a substrate can be located between the carbon-Michael compound and the heat provider, e.g., such that the substrate contacts a portion of the heat provider, and/or a substrate can be located between the carbon-Michael compound and the heat receptor, e.g., such that the substrate contacts a portion of the heat receptor. Differing substrates may be utilized for various applications.

The carbon-Michael compound can be formed in situ. The carbon-Michael compound can be formed, e.g., located, between the heat provider and the heat receptor. For example, components of the carbon-Michael compound, e.g., the multifunctional acrylate compound, multifunctional Michael donor, and optionally each of the catalyst, the blowing agent, the surfactant, and the one or more additives, can be applied to a portion of the heat provider and/or to a portion of the heat receptor whereupon the carbon-Michael compound can be formed from a Michael reaction. Similarly, components of the carbon-Michael compound can be applied to a substrate, e.g., a substrate that contacts a portion of the heat provider, and/or a substrate that contacts a portion of the heat receptor. Components of the carbon-Michael compound can be applied by differing processes for various applications. For example, components of the carbon-Michael compound can be applied by spraying, brushing, rolling, and/or dipping, among other application processes.

As mentioned, surprisingly, it has been found that the carbon-Michael compounds discussed herein can be utilized in high temperature applications, e.g., where the carbon-Michael compounds are exposed to a temperature from 100° C. to 290° C. Embodiments of the present disclosure include locating the carbon-Michael compound between a heat provider and a heat receptor, where the heat provider has a temperature from 100° C. to 290° C. All individual values and subranges from and including 100° C. to 290° C. are included herein and disclosed herein; for example the heat provider can have a temperature with a lower limit of 100° C., 150° C., 200° C., 250° C., or 275° C. to an upper limit of 290° C. For example, the heat provider can have a temperature from 100° C. to 290° C., 150° C. to 290° C., 200° C. to 290° C., 250° C. to 290° C., or 275° C. to 290° C. Advantageously it has been found that the carbon-Michael compounds discussed herein have thermal degradation temperatures that help provide that these carbon-Michael compounds are suitable for the high temperature applications.

The heat provider may be a solid object, a liquid object, a gas object, or a combination thereof. The heat receptor may be a solid object, a liquid object, a gas object, or a combination thereof. Thermal energy can transfer from the heat provider to the heat receptor. The carbon-Michael compound can reduce heat transfer, e.g., from the heat provider to the heat receptor. The heat receptor can have a temperature from 10° C. to 290° C. All individual values and subranges from and including 10° C. to 290° C. are included herein and disclosed herein; for example the heat receptor can have a temperature with a lower limit of 10° C., 20° C., 25° C., 50° C., or 100° C. to an upper limit of 290° C., 285° C., 280, 250° C., or 200° C. For example, the heat receptor can have a temperature from 10° C. to 290° C., 20° C. to 285° C., 25° C. to 280° C., 50° C. to 250° C., or 100° C. to 200° C.

The heat receptor has a temperature that is lower than a temperature of the heat provider. For example, the carbon-Michael compound can be utilized as an insulating material. However, the heat provider and the heat receptor can be in thermal equilibrium, e.g., have the same temperatures, for a time interval. The carbon-Michael compound has the advantage of being used, for example, as a cushioning or a packing material while also being stable at high temperatures (e.g., 200° C.).

For embodiments where the heat provider and the heat receptor are in thermal equilibrium for a time interval the carbon-Michael compound can advantageously be utilized as a cushioning material and/or a packing material, among other applications.

As mentioned, surprisingly, it has been found that the carbon-Michael compounds discussed herein have thermal degradation temperatures that help provide that the carbon-Michael compounds can be utilized in high temperature applications. The carbon-Michael compound can have a thermal degradation temperature from 300° C. to 450° C. All individual values and subranges from 300° C. to 450° C. are included herein and disclosed herein; for example carbon-Michael compound can have a thermal degradation temperature with a lower limit of 300° C., 325° C., or 350° C. to an upper limit of 450° C., 425° C., or 400° C.

The carbon-Michael compound can have differing thicknesses for various applications. For example, for some coating applications the carbon-Michael compound can have a thickness from 1 micron (μm) to 1 centimeter (cm). All individual values and subranges from and including 1 μm to 1 cm are included herein and disclosed herein; for example the carbon-Michael compound can have a thickness with a lower limit of 1 μm, 3 μm, 5 μm, 10 μm, or 20 μm to an upper limit of 1 cm, 0.95 cm, 0.90 cm, 0.80 cm, or 0.75 cm. Also, for example, for some foam insulation applications the carbon-Michael compound can have a thickness from 1 cm to 100 cm. All individual values and subranges from and including 1 cm to 100 cm are included herein and disclosed herein; for example the carbon-Michael compound can have a thickness with a lower limit of 1 cm, 1.5 cm, 2 cm, 3 cm, or 5 cm to an upper limit of 100 cm, 95 cm, 90 cm, 80 cm, or 75 cm.

Additionally, as mentioned, the carbon-Michael compounds can be used in foam insulation applications. It has been found that the carbon-Michael foam products discussed herein have a storage modulus at the high temperature values discussed herein, which are desirable for some applications. The carbon-Michael compounds, e.g., foams, which can have densities of approximately 40 kg/m$^3$ can have a storage modulus at 200° C. from 30 megapascal (MPa) to 1000 MPa. All individual values and subranges from and including 30 MPa to 1000 MPa are included herein and disclosed herein; for example the carbon-Michael compound can have a storage modulus at 200° C. with a lower limit of 30 MPa, 40 MPa, or 50 MPa to an upper limit of 1000 MPa, 950 MPa, or 900 MPa.

EXAMPLES

In the Examples, various terms and designations for materials were used including, for example, the following:

Multifunctional acrylate compound (bisphenol A epoxy diacrylate, product reference CN 120Z, available from Sartomer), multifunctional acrylate compound (di-trimethylolpropane tertraacrylate, product reference SR355, available from Sartomer), multifunctional acrylate compound (ethoxylated (3) bispenol A diacrylate, product reference SR349, available from Sartomer), multifunctional acrylate compound (aromatic urethane acrylate oligomer, product reference CN997, available from Sartomer), multifunctional acrylate compound (bisphenol A glycerolate (1 glycerol/phenol) diacrylate, available from Aldrich), catalyst (1,8-diazabicyclo[5.4.0]undec-7-ene, available from Aldrich), catalyst (1,1,3,3-tetramethylguanidine, available from Aldrich), surfactant (organosilicone surfactant, product reference TEGOSTAB® B 8469, available from Evonik Industries); 1,1,1,3,3-pentafluoropropane (blowing agent, product reference HFC 245fa, available from Honeywell Corporation), Michael donor (multifunctional acetoacetate compound, trimethylolpropane tris acetoacetate, available from Lonza), polyether polyol (product reference Voranol 360, available from The Dow Chemical Company), polyester polyol (product reference Stepanpol PS-3152, available from Stepan), amine catalyst (product reference Polycat 5, available from Air Products), amine catalyst (product reference Polycat 8, available from Air Products), surfactant (product reference L-6900, available from Momentive), polymethylene polyphenylisocyanate (product reference PAPI 27, available from The Dow Chemical Company).

Carbon-Michael Compound 1

Carbon-Michael compound 1 was prepared as follows. Bisphenol A glycerolate (1 glycerol/phenol) diacrylate (15.00 grams) was heated to 60° C. The pre-heated bisphenol A glycerolate (1 glycerol/phenol) diacrylate, SR355 (15.00 grams), 1,8-diazabicyclo[5.4.0]undec-7-ene (1.24 grams) and TEGOSTAB® B 8469 (0.46 grams) were added to a container and mechanically stirred for two minutes at approximately 900 rotations per minute. HFC 245fa (8.82 grams) was added to the contents of the container, which were mechanically stirred for an additional two minutes at approximately 900 rotations per minute. With stirring paused, trimethylolpropane tris acetoacetate (14.02 grams) was added to the contents of the container, then the contents of the container were mechanically stirred for 30 seconds at approximately 2500 rotations per minute to provide carbon-Michael compound 1.

Carbon-Michael Compound 2

Carbon-Michael compound 2 was prepared as follows. SR355 (15.00 grams), SR349 (15.00 grams), 1,8-diazabicyclo[5.4.0]undec-7-ene (0.84 grams) and TEGOSTAB® B 8469 (0.45 grams) were added to a container and mechanically stirred for two minutes at approximately 900 rotations per minute. HFC 245fa (8.85 grams) was added to the contents of the container, which were mechanically stirred for an additional two minutes at approximately 900 rotations per minute. With stirring paused, trimethylolpropane tris acetoacetate (14.18 grams) was added to the contents of the container, then the contents of the container were mechanically stirred for 30 seconds at approximately 2500 rotations per minute to provide carbon-Michael compound 2.

Carbon-Michael Compound 3

Carbon-Michael compound 3 was prepared as follows. SR355 (15.00 grams), CN997 (15.00 grams), 1,8-diazabicyclo[5.4.0]undec-7-ene (1.12 grams) and TEGOSTAB® B 8469 (0.53 grams) were added to a container and mechanically stirred for two minutes at approximately 900 rotations per minute. HFC 245fa (9.81 grams) was added to the contents of the container, which were mechanically stirred for an additional two minutes at approximately 900 rotations per minute. With stirring paused, trimethylolpropane tris acetoacetate (18.93 grams) was added to the contents of the container, then the contents of the container were mechanically stirred for 30 seconds at approximately 2500 rotations per minute to provide carbon-Michael compound 3.

Carbon-Michael Compound 4

Carbon-Michael compound 4 was prepared as follows. CN102Z (160.00 grams) was heated to 60° C. The preheated CN120Z, SR355 (80.00 grams), 1,1,3,3-tetramethylguanidine (5.60 grams) and TEGOSTAB® B 8469 (5.48 grams) were added to a container and mechanically stirred for two minutes at approximately 900 rotations per minute. HFC 245fa (73.05 grams) was added to the contents of the container, which were mechanically stirred for an additional two minutes at approximately 900 rotations per minute. With stirring paused, trimethylolpropane tris acetoacetate (125.27 grams) was added to the contents of the container, then the contents of the container were mechanically stirred for 30 seconds at approximately 2500 rotations per minute to provide carbon-Michael compound 4.

Polyurethane Foam

A polyurethane foam was prepared as follows. Voranol 360 (15.63 grams), Stepanpol PS-3152 (3.91 grams), Polycat 5 (0.20 grams), Polycat 8 (0.29 grams), and L-6900 (0.39 grams) were added to a container and mechanically stirred for two minutes at approximately 900 rotations per minute. Water (0.39 grams) and HFC 245fa (5.86 grams) were added to the contents of the container, which were mechanically stirred for an additional two minutes at approximately 900 rotations per minute. With stirring paused, PAPI 27 (24.33 grams) was added to the contents of the container, then the contents of the container were mechanically stirred for approximately 5 seconds at approximately 2500 rotations per minute to provide the polyurethane foam.

Thermogravimetric analysis was performed on the carbon-Michael compounds 1, 2, 3, and 4 and the polyurethane foam via a TA Instruments model Q5000 TGA. The thermogravimetric analysis was run under nitrogen from 20° C. to 500° C. with a temperature ramp rate of 10° C. per minute. Oneset thermal degradation temperatures as determined by the thermogravimetric analysis are reported in Table 1.

TABLE 1

| | Carbon-Michael compound 1 | Carbon-Michael compound 2 | Carbon-Michael compound 3 | Carbon-Michael compound 4 | Polyurethane foam |
|---|---|---|---|---|---|
| Onset thermal degradation temperature (° C.) | 355.0 | 365.5 | 361.0 | 374.0 | 258.6 |

The data in Table 1 show that each of the carbon-Michael compounds 1, 2, 3 and 4 has an oneset thermal degradation temperature greater than 350° C., which indicates that the carbon-Michael compounds are suitable for high temperature applications. The data in Table 1 shows that each of the carbon-Michael compounds 1, 2, 3 and 4 has an improved oneset thermal degradation temperature as compared to the polyurethane foam.

Dynamic mechanical analysis was performed on the carbon-Michael compounds 1, 2, 3, and 4 and the polyurethane foam via a TA Instruments RSA III Rheometer having compression chamber. A cylindrical sample (11 millimeter long, 21 millimeter diameter) of each of the carbon-Michael compounds 1, 2, 3, and 4 and the polyurethane foam was respectively placed in the compression chamber. The dynamic mechanical analysis was run from −100° C. to 200° C. with a temperature ramp rate of 3° C. per min and an applied frequency of 1 Hz. Storage moduli as determined by the dynamic mechanical analysis are reported in Table 2.

TABLE 2

| | Carbon-Michael compound 1 | Carbon-Michael compound 2 | Carbon-Michael compound 3 | Carbon-Michael compound 4 | Polyurethane foam |
|---|---|---|---|---|---|
| Storage modulus at 25° C. (pascal) | 6.78E+05 | 8.27E+05 | 1.38E+06 | 5.14E+05 | 2.40E+05 |
| Storage modulus at 200° C. (pascal) | 3.66E+04 | 5.01E+04 | 3.01E+05 | 5.04E+05 | 2.01E+04 |

The data in Table 2 shows that each of the carbon-Michael compounds 1, 2, 3, and 4 has a storage modulus at 200° C. greater than 30 megapascal, which indicates that the carbon-Michael compounds are suitable for high temperature applications. The data in Table 2 shows that each of the carbon-Michael compounds 1, 2, 3, and 4 has an improved storage modulus at 200° C. as compared to the polyurethane foam.

Example 1

Example 1, a method of using a carbon-Michael compound to reduce heat transfer, was performed as follows. Carbon-Michael compound 4 was cut to a 7 inch by 7 inch square and 1 inch thick sample. One side of the sample was placed on a flat surface of a 6 inch by 6 inch hot plate, which was pre-heated to 250° C. A thermal couple was put on the other side of the sample. The temperature monitored by the thermal couple slowly increased from room temperature to about a temperature plateau at 65° C. within 2 hours. The shape and dimension of the sample remained unchanged at 250° C. for 4 hours as determined by visual inspection. Example 1 illustrates that the carbon-Michael compounds are suitable for high temperature applications.

What is claimed:

1. A method of using a carbon-Michael compound to reduce heat transfer comprising:
    locating the carbon-Michael compound between a heat provider and a heat receptor, wherein
    the carbon-Michael compound is a reaction product of a multifunctional acrylate compound with a multifunctional Michael donor;
    the heat provider has a temperature from 100° C. to 290° C.; and
    the carbon-Michael compound is a closed-cell foam.

2. The method of claim 1, wherein the multifunctional acrylate compound and the multifunctional Michael donor are reacted in a molar ratio of 0.5:3.0 to 3.0:0.5 moles of multifunctional acrylate compound functionalities to moles of the Michael donor functionalities.

3. The method of claim 1, wherein the multifunctional acrylate compound selected from the group of trimethylolpropanetriacrylate, pentaerythritoltetraacrylate, di-trimethylolpropanetertraacrylate, di-pentaerythritolhexaacrylate, di-pentaerthritolpentaacrylate, diacrylate of diglycidyl ether bisphenol-A, ethoxylated trimethylolpropane triacrylate, tricyclodecanedimethanol diacrylate, and cyclohexanedimethanol diacrylate, and combinations thereof.

4. The method of claim 1, wherein the multifunctional Michael donor is selected from the group of acetoacetates derived from glycerol, trimethylolpropane, ethanol isosorbide, neopentylglycol, pentaerythritol, di-methylolpropane, di-pentaerythritol, propoxylated monosaccharides, trimethylol ethane, or a combination thereof.

5. The method of claim 1, wherein the multifunctional acrylate compound and the multifunctional Michael donor are reacted in the presence of a surfactant, wherein the surfactant has a concentration of 0.1 weight percent to 5.0 weight percent based upon a total weight of the multifunctional Michael donor and the multifunctional acrylate compound.

6. A method of using a carbon-Michael compound to reduce heat transfer comprising:
   locating the carbon-Michael compound between a heat provider and a heat receptor, wherein
      the carbon-Michael compound is a reaction product of a multifunctional acrylate compound with a multifunctional Michael donor;
      the heat provider has a temperature from 100° C. to 290° C.; and
      the multifunctional acrylate compound and the multifunctional Michael donor are reacted in the presence of a blowing agent selected from the group of cyclopentane, n-pentane, formaldehyde dimethylacetal, methylformate, methyl butane, 1,1,2,2,3-pentafluoropropane, 1,1,1,3,3-pentafluoropropane, 1,1,1,3,3-pentafluorobutane, 1,1,1,2,3,4,4,5,5,5-decafluoropentane, cis-1,1,1,4,4,4-hexafluorobut-2-ene, trans-1-chloro-3,3,3-trifluoropropene, or a combination thereof, wherein the blowing agent has a concentration of a lower limit of 0.5 weight percent to an upper limit of 50 weight percent blowing agent based upon a total weight of the multifunctional Michael donor and the multifunctional acrylate compound.

7. The method of claim 6, wherein the carbon-Michael compound has a thermal degradation temperature from 300° C. to 450° C.

8. The method of claim 6, wherein the multifunctional acrylate compound and the multifunctional Michael donor are reacted in the presence of a catalyst selected from the group of 1,1,3,3-tetramethylguanidine, 1,8-diazabicyclo[5.4.0]undec-7-ene, 1,5-diazabicyclo[4.3.0]non-5-ene, tetramethylammonium hydroxide, (2-hydroxyethyl)trimethylammonium hydroxide, potassium hydroxide, potassium carbonate, potassium phosphate, potassium phenoxide, sodium phenoxide, tetraethylammonium hydroxide, or a combination thereof, wherein the catalyst has a concentration of 0.001 moles of catalyst per equivalent of multifunctional Michael donor to 1 mole of catalyst per equivalent of multifunctional Michael donor.

* * * * *